United States Patent
Kaneblei

[11] Patent Number: 5,889,195
[45] Date of Patent: Mar. 30, 1999

[54] MEASURING ARRANGEMENT FOR DETERMINING THE CONCENTRATION OF GASES FROM LIQUID MEDIA

[75] Inventor: Ingo Kaneblei, Lübeck, Germany

[73] Assignee: Drägerwerk AG, Lübeck, Germany

[21] Appl. No.: 909,757

[22] Filed: Aug. 12, 1997

[30] Foreign Application Priority Data

Feb. 12, 1997 [DE] Germany .................. 197 05 195.2

[51] Int. Cl.$^6$ .............. A61B 5/00; G01N 7/00; G01N 13/04
[52] U.S. Cl. ............. 73/19.12; 73/64.47; 73/19.01; 422/82
[58] Field of Search .............. 73/19.12, 19.01, 73/64.47, 31.07

[56] References Cited

U.S. PATENT DOCUMENTS

| | | | |
|---|---|---|---|
| 3,662,604 | 5/1972 | Low et al. | 73/421.5 R |
| 3,929,003 | 12/1975 | Llewellyn | 73/61 R |
| 4,474,051 | 10/1984 | Fukuda et al. | 73/19 |
| 4,860,577 | 8/1989 | Patterson | 73/64.3 |
| 4,998,432 | 3/1991 | Plessers et al. | 73/19.07 |
| 5,012,672 | 5/1991 | Mckee | 73/31.07 |
| 5,058,416 | 10/1991 | Engelhartd et al. | 73/19.01 |
| 5,183,760 | 2/1993 | Sweetana et al. | 435/285 |
| 5,235,843 | 8/1993 | Langhorst | 73/19.02 |
| 5,499,531 | 3/1996 | Henderson | 73/64.45 |

OTHER PUBLICATIONS

Drägerwerk AG 1996 *Measurement of Contaminants in Liquids with the DLE–Kit Environmental Monitoring*.
Drägerwerk AG 1996 *Analytik von Schadstoffen in flüssigen Proben* equivalent to above text.

*Primary Examiner*—Hezron E. Williams
*Assistant Examiner*—J. David Wiggins
*Attorney, Agent, or Firm*—McGlew and Tuttle

[57] ABSTRACT

A measuring arrangement for determining the concentration of gases dissolved in a liquid is proposed, which has a simple design and makes possible the use of known gas-measuring apparatus based on color reaction tubes or color reaction capillaries. A preferably flexible tube-like body is provided which is formed of a material that is permeable to the gases to be measured but is impermeable to the liquid. A carrier gas flows on the inside of this body and the body is connected to the gas-measuring apparatus upstream in the direction of the gas flow. The semipermeable material is preferably microporous polytetrafluoroethylene (PTFE).

19 Claims, 1 Drawing Sheet

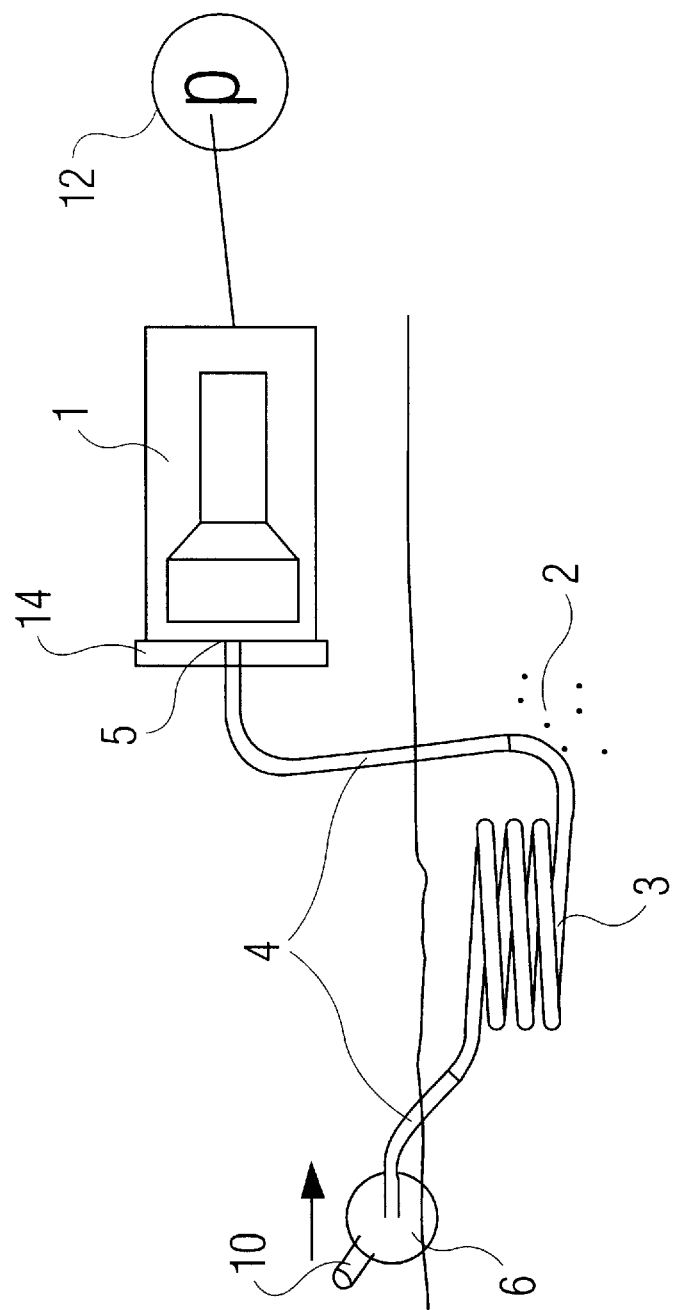

ered structure. The flexible tube-like body is preferably made of a microporous material which is impermeable to water, such as PTFE.

MEASURING ARRANGEMENT FOR DETERMINING THE CONCENTRATION OF GASES FROM LIQUID MEDIA

FIELD OF THE INVENTION

The present invention pertains to a measuring arrangement for determining the concentration of gases from a liquid medium with a gas-measuring apparatus and an associated gas delivery unit.

BACKGROUND OF THE INVENTION

Such measurements, e.g., the "Dräger DLE Method," are currently carried out by allowing a carrier gas, e.g., air, to flow through a sample of the liquid containing the gas to be measured in a wash bottle, so that the carrier gas takes up the gaseous substance to be measured, especially a volatile harmful substance. The carrier gas may be passed first through a prefilter, especially an activated carbon tube, for precleaning, and it is then pumped by means of a pump to the gas-measuring apparatus, and the wash bottle with the liquid sample, through which the pure carrier flows, is arranged between the prefilter and the gas-measuring apparatus. The immersion tube of the wash bottle is provided with a frit in order to achieve a fine distribution of the gas in the liquid and consequently the highest possible degree of saturation of the carrier gas. The saturation of the carrier gas with the gas to be determined depends on various parameters, especially the size of the gas bubbles, the temperature, and the residence time in the liquid. Special devices, individual calibration, and correction at the time of the evaluation of the measurement results are necessary as a result. A more detailed description of this can be found in the Dräger inhouse publication *Analytik von Schadstoffen in flüssigen Proben* [Analysis of Harmful Substances in Liquid Samples]. The determination of the gas concentration proper is carried out in a gas-measuring apparatus, especially one comprising a visually or optoelectronically scanned test tube with a color reaction zone providing a substance-specific and concentration-dependent display, wherein the length of the change in color indicated is usually an indicator of the concentration of the gas to be detected.

SUMMARY AND OBJECTS OF THE INVENTION

The primary object of the present invention is to provide a measuring arrangement of a simple design without a wash bottle for determining the concentration of gases from a liquid medium.

According to the invention, a measuring arrangement is provided for determining the concentration of gases from a liquid medium with a gas-measuring apparatus and an associated gas delivery unit. A body, which comprises a material that is permeable to the gases to be measured but is impermeable to the liquid and through which a carrier gas flows on the inside, is connected to the gas-measuring apparatus upstream when viewed in the direction of gas flow.

The body is preferably a flexible tube-like body, consisting essentially of a microporous material impermeable to water. This flexible tube-like body is preferably formed of polytetrafluoroethylene (PTFE).

The flexible tube-like body extends in the liquid and is connected to a carrier gas source, especially ambient air, via an opening that is located opposite in relation to the gas-measuring apparatus. The flexible tube-like body may be connected to the gas-measuring apparatus with a first gas-tight flexible tube section via a gas inlet and may be connected by a second gas-tight flexible tube section to a float body floating on the liquid and to the carrier gas source.

The gas delivery unit may be arranged downstream of the gas-measuring apparatus in the direction of the gas flow.

At least one chemically reactive, gas-selective prefilter may arranged upstream of the gas-measuring apparatus in order to retain the other gases of a gas mixture which interfere with the determination of the concentration of a certain gas.

One essential advantage of the present invention is that the gas-measuring apparatus known for the determination of the concentration of gas components can also be used to determine the concentration of gases dissolved in a liquid medium with a simple arrangement of a flexible tube-like body made of a semipermeable material, which arrangement is arranged upstream of the apparatus. The semipermeable material does not allow the liquid phase to pass through, but it lets the gas to be measured pass through. The measuring arrangement according to the present invention has a volume, through which medium can flow and is made of a semipermeable material, especially a microporous flexible tube consisting of PTFE (polytetrafluoroethylene) or a flexible tube-like body, which is arranged in the liquid to be investigated such that the outer surface is wetted by the liquid, and a carrier gas, especially air or nitrogen or even a noble gas, flows through the inside. The flexible tube wall thus forms the phase boundary. Due to the partial pressure gradient, the carrier gas is charged with the gas to be determined, which is contained in the liquid, in the flexible tube-like body. The degree of saturation depends essentially only on parameters which are easy to set, namely, the size of the outer surface of the flexible tube wall that is in contact with the liquid, the gas volume flow being delivered, as well as the temperature. The parameters, which cannot be influenced or are difficult to influence according to the prior-art process with wash bottle, such as the size of the air bubbles, the depth of immersion of the frit into the liquid, as well as the frit itself, are eliminated. An individual calibration of the wash bottle can thus be omitted. The carrier gas is consequently charged more or less intensely, depending essentially on the concentration of the gas to be detected in the liquid. Another favorable effect is achieved due to the length of the flexible tube-like body, through which the medium flows. The longer this body, the sooner will an enrichment with the gas to be determined be achieved inside the flexible tube-like body in the direction of the flow of the carrier gas, until saturation is reached. A very simple and accurate measurement method is offered especially by the concentration determination of the gas to be detected by means of a gas-measuring apparatus arranged downstream on the basis of optoelectronically scanned color reaction tubes or color reaction capillaries, because the volume needed for the measurement is extremely small and the ratio of the gas volume to be delivered to the area of the semipermeable, flexible tube-like body is consequently very small. The suitable semipermeable materials include especially microporous materials based on PTFE (polytetrafluoroethylene), which are impermeable to the liquid medium, namely, generally water, but are permeable to the gases or vapors to be measured. The semipermeable material is physically embodied as a flexible tube-like body, which may be a tube, a flexible tube, or even a bundle of parallel hollow fibers. It would also be possible to design the flexible tube-like body in the form of an essentially two-dimensional, plate-like module, or in the form of a meandering or labyrinth-like, divided flexible tube section. A plurality of flexible tube sections in parallel may optionally be used as well. It is essential for the largest possible outer wall surface of the flexible tube-like body or of the module to be in contact with the liquid medium containing the gas to be detected or to immerse into the said medium. The arrangement according to the present invention is also suitable for determining the concentration of correspondingly charged soils, e.g., for extracting gas from a solid medium of landfills or sludge-containing areas.

The present invention will be explained below on the basis of an exemplary embodiment of a measuring arrangement according to the present invention represented schematically in the drawing.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a schematic view of a measuring arrangement according to the invention for determining the concentration of gases from a liquid medium with a gas-measuring apparatus.

DESCRIPTION OF THE PREFERRED EMBODIMENT

Referring to the drawing in particular, the invention comprises a measuring arrangement for the direct measurement of a gas, e.g., $H_2S$, which is dissolved in a liquid medium, especially water. The gas-measuring apparatus 1 is in the immediate vicinity of the transducer proper, e.g., at the edge of a liquid 2 to be investigated. A flexible tube-like body 3 consisting of microporous, semipermeable PTFE is located in the liquid 2, which is generally water. One gas-permeable flexible tube section 4 each connects the flexible tube-like body 3 to the gas-measuring apparatus 1 via a gas inlet 5, on the one hand, and the flexible tube-like body 3 to the ambient air via a float body 6, on the other hand. The outer surface of the flexible tube-like body 3 is completely in contact with liquid 2, and the flexible tube sections 4 join it in the liquid 2, as is indicated in the figure. The ambient air is used as the carrier gas in this case. The carrier gas enters an intake 10 and is delivered through the measuring arrangement and ultimately into the gas-measuring apparatus 1 in the direction of flow indicated by the arrow at the float body 6 by means of a pump 12. The pump is integrated therein or is arranged downstream as shown in the FIGURE The gas to be detected, which is dissolved in the liquid 2, flows into the flexible tube-like body 3, which is permeable to this gas, based on an established partial pressure gradient. The gas to be detected is then transported by the carrier gas, here air, to the gas-measuring apparatus 1. The larger the effective surface area of the flexible tube-like body at a given temperature, i.e., the length of the flexible tube at a given flexible tube diameter, and the smaller the gas volume flow, the sooner will the degree of saturation of the carrier gas with the gas to be measured be reached. The measurement of the concentration of the gas to be determined takes place in the gas-measuring apparatus 1. This is preferably a measuring system with optoelectronic evaluation of the gas-specific color reaction zone operating on the basis of color reaction tubes, but especially on the basis of color reaction capillaries. The length of the zone of the color change at a predetermined gas volume is, in general, in a linear relationship to the concentration of the gas to be determined, and the concentration can thus be quantitatively determined. Depending on the composition of a gas of different components, it may be meaningful to provide substance-specific, chemically selective prefilters 14 in front of the gas-measuring apparatus in the connecting flexible tube or in the gas inlet 5 of the gas-measuring apparatus 1 in order to rule out incorrect measurements due to cross sensitivities of the measurement method to various other, interfering gas components. Such prefilters guarantee that only the gas to be measured will ultimately reach the gas-measuring apparatus 1 with the carrier gas.

Experiments with an arrangement as described above led to good results in the case of the measurement of the concentration of $H_2S$ in water; these results made possible a more sensitive resolution with respect to low concentrations than with the method with wash bottle known from the state of art. The measurements were performed in this case with a gas volume flow of 15 mL per minute with a microporous PTFE flexible tube with a diameter of at least 3 mm and a length of about 50 to 70 cm. When usual color reaction tubes were used, good results were obtained even with a microporous PTFE flexible tube having a diameter of at least 4 mm and a length of about 100 to 120 cm.

Good results were also obtained with a tube-like body 3 made of a PTFE membrane material with an inner diameter of 2 millimeters, an outer diameter of 3 millimeters, a porosity of 71.2% and the length of 1 meter. Such a tube-like body 3 can be obtained from the supplier SUMITOMO, TB 342-07, mV. Another material for the tube-like body 3 is polypropylene capillary tube with an inner diameter of 1.8 millimeters, an outer diameter of 2.7 millimeters, a pore size of 0.2 micrometers and a length of 1.25 meters. Such a tube can be obtained from the supplier AKZO Nobel, S 6/2 mV, type 6/2. Generally, the membrane materials with a pore size of from 0.2 micrometers to 1.2 micrometers show the best results. A pore size of from 0.2 micrometers to 1.6 micrometers may also be useful. To measure $H_2S$ in water or benzole in water, the tube obtained from AKZO Nobel was used for the body 3. To measure $NH_3$ in water, the above mentioned SUMITOMO material was used. Concentrations in the range of 0.05 to 6 mg gas per liter water could be measured, specifically:

$H_2S$ in water: 0.05 to 6 mg $H_2S$/liter water $NH_3$ in water: 0.05 to 0.3 mg $NH_3$/liter water Benzole in water: 0.05 to 0.3 mg benzole/liter water.

While a specific embodiment of the invention has been shown and described in detail to illustrate the application of the principles of the invention, it will be understood that the invention may be embodied otherwise without departing from such principles.

What is claimed is:

1. A measuring arrangement for determining the concentration of gases from a liquid medium with a gas-measuring apparatus and an associated gas delivery unit, the arrangement comprising:

a flexible tube-like body including a material that is permeable to the gases to be measured but is impermeable to the liquid and through which a carrier gas flows on an inside flow region in fluid communication with a carrier gas source, said body being connected to the gas-measuring apparatus upstream with respect to a direction of gas flow;

a first gas-tight interconnection flexible tube section;

a second gas-tight interconnection flexible tube section; and a float body floating on said liquid, said flexible tube-like body is connected to the gas-measuring apparatus with said first gas-tight flexible tube section via a gas-measuring apparatus gas inlet and is connected by said second gas-tight flexible tube section to said float body and to said carrier gas source.

2. The measuring arrangement in accordance with claim 1, wherein said body is a flexible tube-like body formed of a microporous material impermeable to water.

3. The measuring arrangement in accordance with claim 2, wherein said flexible tube-like body consists essentially of polytetrafluoroethylene (PTFE).

4. The measuring arrangement in accordance with claim 2, wherein said flexible tube-like body extends in said liquid and is connected to a carrier gas source via an opening that is located opposite in relation to the gas-measuring apparatus.

5. The measuring arrangement in accordance with claim 4, wherein said carrier gas source is ambient air.

6. The measuring arrangement in accordance with claim 1, wherein the gas delivery unit is arranged downstream of the gas-measuring apparatus in the direction of the gas flow.

7. The measuring arrangement in accordance with claim 1, further comprising:

at least one chemically reactive, gas-selective prefilter arranged upstream of the gas-measuring apparatus, said prefilter retaining one or more gases of a gas, which one or more gasses interfere with a determination of the concentration of a certain gas.

8. A device for determining the concentration of gases from a liquid medium, comprising:

a gas-measuring apparatus;

a gas delivery unit associated with said gas measuring apparatus; and a body immersed in the liquid medium to define an inside gas flow region and an outer peripheral surface in contact with the liquid medium, said body being formed of a material that is permeable to the gases to be measured but is impermeable to the liquid and through which a carrier gas flows on said inside, said gas delivery unit being connected to said body to provide a flow of a carrier gas through said body in a flow direction and establishing a partial pressure gradient forcing gas to be detected, which is dissolved in the liquid medium, to flow through said material, that is permeable to the gases to be measured but is impermeable to the liquid, into said body, said body being connected to said gas-measuring apparatus with said body upstream of said gas-measuring apparatus with respect to said direction of gas flow.

9. The device in accordance with claim 8, wherein said body is a flexible tube-like body formed of a microporous material impermeable to water.

10. The device in accordance with claim 9, wherein said flexible tube-like body comprises polytetrafluoroethylene (PTFE).

11. The device in accordance with claim 9, wherein said flexible tube-like body extends in said liquid and is connected to a carrier gas source via an opening that is located opposite in relation to the gas-measuring apparatus.

12. The device in accordance with claim 11, wherein said carrier gas source is ambient air.

13. The device in accordance with claim 12, wherein said gas delivery unit includes a first gas-tight flexible tube interconnection section and a second gas-tight flexible tube interconnection section; and the device further comprising:

a float body floating on said liquid, said flexible tube-like body is connected to said gas-measuring apparatus with said first gas-tight flexible tube section via a gas-measuring apparatus gas inlet and is connected by said second gas-tight flexible tube section to said float body and to said carrier gas source.

14. The device in accordance with claim 8, wherein said gas delivery unit is arranged downstream of said gas-measuring apparatus in the direction of the gas flow.

15. The device in accordance with claim 8, further comprising:

at least one chemically reactive, gas-selective prefilter arranged upstream of said gas-measuring apparatus, said prefilter retaining one or more gases of a gas mixture, which one or more gasses interfere with a determination of the concentration of a certain gas.

16. The device in accordance with claim 11, further comprising:

providing a first gas-tight flexible tube section;

providing a second gas-tight flexible tube section; and a float body floating on said liquid, said flexible tube-like body is connected to said gas-measuring apparatus with said first gas-tight flexible tube section via a gas-measuring apparatus gas inlet and is connected by said second gas-tight flexible tube section to said float body and to said carrier gas source.

17. A process for determining the concentration of gases from a liquid medium, comprising:

providing a body including a material that is permeable to the gases to be measured but is impermeable to the liquid medium, the body defining an interior gas flow passage and an outer peripheral surface;

immersing the body in the liquid medium such that the outer peripheral surface is in contact with the liquid medium;

connecting a gas delivery unit to the immersed body and establishing a flow of carrier gas through the body and establishing a partial pressure gradient forcing gas to be detected, which is dissolved in the liquid medium, to flow through said material, that is permeable to the gases to be measured but is impermeable to the liquid, into said body;

connecting said body to a gas-measuring apparatus for receiving carrier gas and gas to be detected which leaves said interior gas flow passage and for determining the concentration of the gas to be detected in the liquid medium.

18. The process according to claim 17, wherein:

said body is provided as a flexible tube-like body formed of a microporous material impermeable to water, and said flexible tube-like body comprises polytetrafluoroethylene (PTFE).

19. The process in accordance with claim 17, wherein said carrier gas source is ambient air and further comprising providing at least one chemically reactive, gas-selective prefilter arranged upstream of said gas-measuring apparatus, said prefilter retaining one or more gases of a gas mixture, which one or more gasses interfere with a determination of the concentration of a certain gas.

* * * * *